United States Patent
Matsumura et al.

(10) Patent No.: US 9,826,732 B2
(45) Date of Patent: Nov. 28, 2017

(54) COMPOSITION FOR CRYOPRESERVATION OF CELLS AND TISSUES

(71) Applicant: Bio Verde Inc., Kyoto-shi, Kyoto (JP)

(72) Inventors: Kazuaki Matsumura, Kyoto (JP); Hajime Sugai, Hirakata (JP); Suong-Hyu Hyon, Uji (JP)

(73) Assignee: Bio Verde Inc., Kyoto-shi, Kyoto (JP)

( * ) Notice: Subject to any disclaimer, the term of this patent is extended or adjusted under 35 U.S.C. 154(b) by 0 days.

(21) Appl. No.: 15/199,954

(22) Filed: Jun. 30, 2016

(65) Prior Publication Data

US 2016/0309706 A1    Oct. 27, 2016

Related U.S. Application Data

(62) Division of application No. 14/266,236, filed on Apr. 30, 2014, now Pat. No. 9,603,355, which is a division of application No. 13/001,237, filed as application No. PCT/JP2009/002941 on Jun. 26, 2010, now abandoned.

(30) Foreign Application Priority Data

Jun. 27, 2008  (JP) ................... 2008-169183
Sep. 8, 2008   (JP) ................... 2008-230005

(51) Int. Cl.
*A01N 1/02* (2006.01)
*C12N 5/071* (2010.01)
*A23L 3/375* (2006.01)
*A61K 47/34* (2017.01)

(52) U.S. Cl.
CPC ............ *A01N 1/0221* (2013.01); *A23L 3/375* (2013.01); *A61K 47/34* (2013.01); *C12N 5/0602* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,670,308 | A | 9/1997 | Geraci et al. |
| 5,759,764 | A | 6/1998 | Polovina |
| 6,140,121 | A | 10/2000 | Ellington et al. |
| 6,740,643 | B2 | 5/2004 | Wolff et al. |
| 7,033,607 | B2 | 4/2006 | Trubeskoy et al. |
| 7,090,846 | B2 | 8/2006 | Szego |
| 2005/0053911 | A1 | 3/2005 | Greener et al. |
| 2005/0265979 | A1 | 12/2005 | Aoki et al. |
| 2006/0257539 | A1 | 11/2006 | Zheng et al. |
| 2008/0317704 | A1 | 12/2008 | Obata et al. |
| 2009/0142830 | A1 | 6/2009 | Yamashiro et al. |
| 2009/0275066 | A1 | 11/2009 | Popot et al. |
| 2011/0172315 | A1 | 7/2011 | Matsumura et al. |
| 2014/0243426 | A1 | 8/2014 | Matsumura et al. |

FOREIGN PATENT DOCUMENTS

| | | |
|---|---|---|
| EP | 3246824 A2 | 11/1987 |
| EP | 1723857 A1 | 11/2006 |
| JP | 5040326 B2 | 2/1993 |
| JP | H10146168 A | 6/1998 |
| JP | H10-511402 A | 11/1998 |
| JP | 2001247401 A | 9/2001 |
| JP | 2003-171463 A | 6/2003 |
| JP | 2003-250506 A | 9/2003 |
| JP | 2003267801 A | 9/2003 |
| JP | 2005-126533 A | 5/2005 |
| JP | 3694730 B2 | 9/2005 |
| JP | 2005-318815 A | 11/2005 |
| JP | 2007141647 A | 6/2007 |
| JP | 2008-041596 A | 2/2008 |
| WO | 9714785 A2 | 4/1997 |
| WO | 2008058963 A1 | 5/2008 |
| WO | 2010079058 A2 | 7/2010 |

OTHER PUBLICATIONS

Lovelock JE and Bishop MWH, Nature 183: 1394-1395, 1959.
Polge C., Smith AU, 164:666 Parkes AS, Nature-666, 1949.
Miszta-Lane H, Gill P, Mirbolooki M, Lakey JRT. Cell Presery Technol Reproduction 20, 1779-1786, 2005.
Ha SY, Jee BC, Suh CS, Kim HS, Oh SK, Kim SH, Moon SY. Human Reproduction 20, 1779-1786, 2005.
Yu HN, Lee YR, Noh EM, et al. Int J. Hematol, 87: 189-194; 2008.
Adler S, Pellozzer C, Paparella M, Hartung T, Bremer S. Toxicol in Vitro 20 265-271, 2006.
Tribet et al.; PNAS vol. 93, pp. 15047-15050, 1996.
Arav et al.; Molecular Reproduction and Development vol. 36, pp. 488-493, 1993.
Scott et al.; J Mol Evol V, 27 pages, pp. 29-35, 1988.

*Primary Examiner* — Richard A Schnizer
*Assistant Examiner* — Katherine Peebles
(74) *Attorney, Agent, or Firm* — United IP Counselors, LLC

(57) ABSTRACT

A composition for cryopreservation of cells and tissues of human and other animals in a safe manner without using toxic substances such as DMSO, as well as for freeze preserving or freeze-drying of foods and pharmaceuticals. In embodiments, ε-poly-L-lysine is reacted with succinic anhydride so that 60% or more of amino groups are blocked; and, thus obtained polymer compound is added to Dulbecco-modified eagle MEM culture medium (DMEM) on market sale to form a cryopreservation liquid. In embodiments for foods or pharmaceuticals, the ε-poly-L-lysine derivative was added by 0.5-10 wt % to curb freeze concentration.

4 Claims, 3 Drawing Sheets

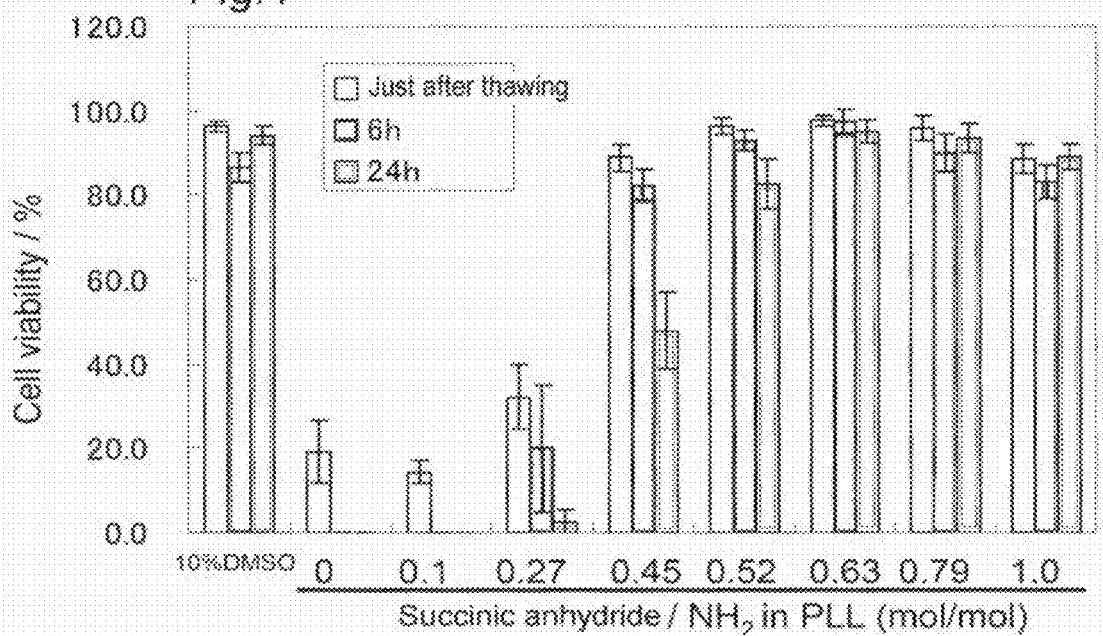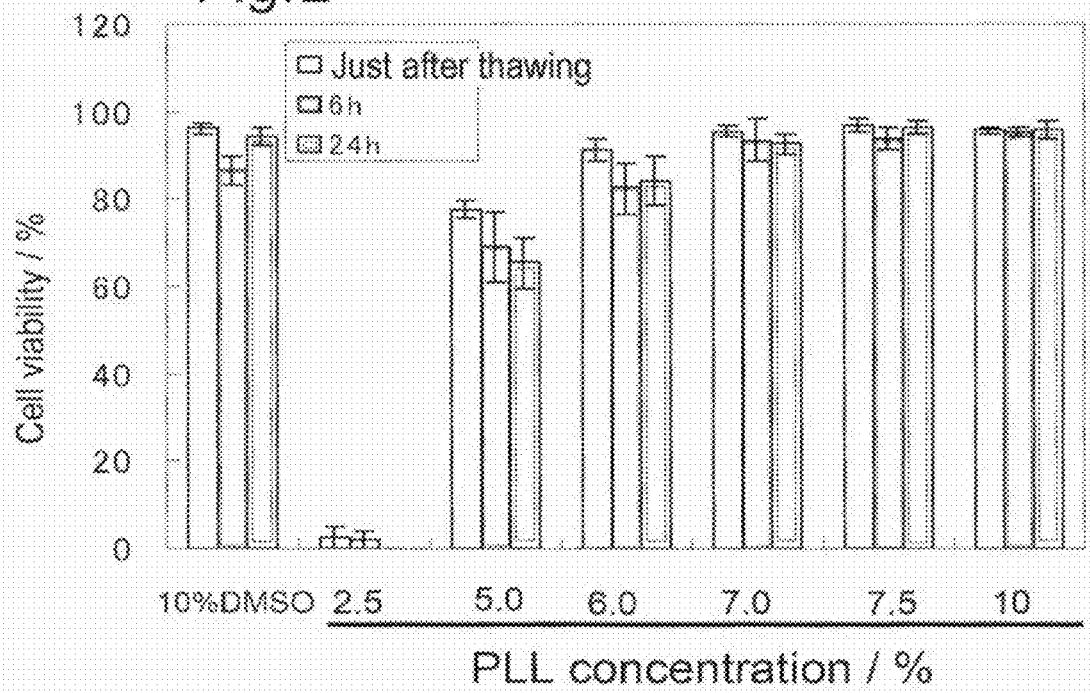

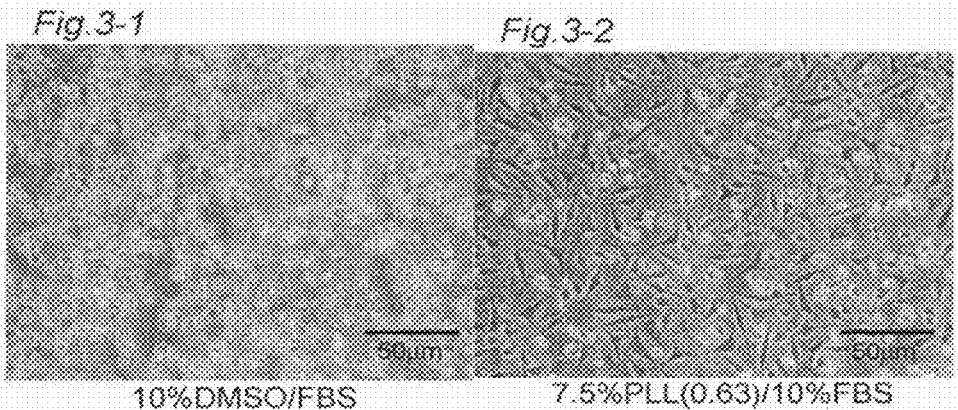
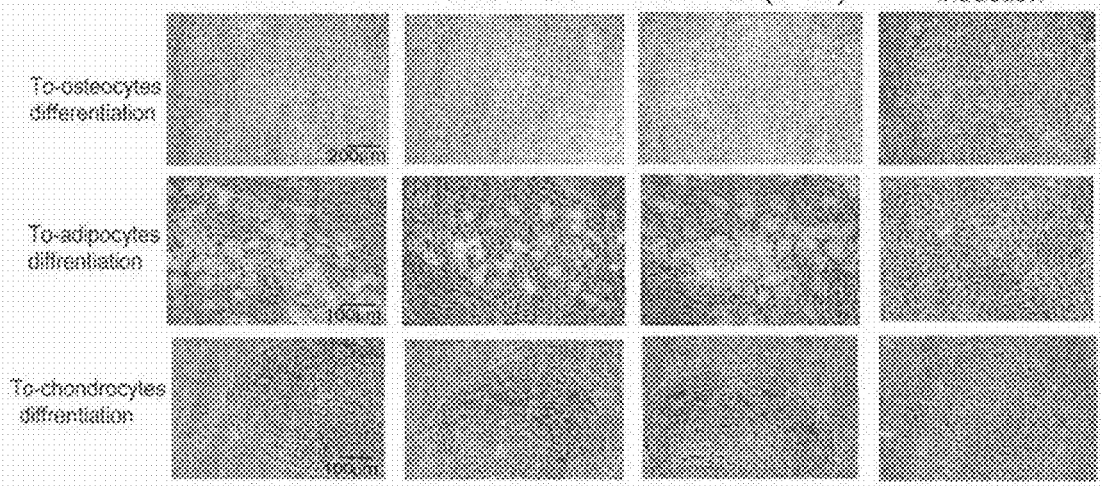

COMPOSITION FOR CRYOPRESERVATION OF CELLS AND TISSUES

CROSS-REFERENCE TO RELATED APPLICATIONS

This application is a divisional application of Ser. No. 14/266,236, filed on Apr. 30, 2014. That application is a divisional application of Ser. No. 13/001,237, filed on Dec. 23, 2010, which is the U.S. National Phase of PCT International Application No. PCT/JP2009/002941, filed on Jun. 26, 2009, and claims priority to Japanese Patent Application No. 2008-169183, filed on Jun. 27, 2008, and Japanese Patent Application No. 2008-230005, filed on Sep. 8, 2008. The contents of these applications are herein incorporated by reference in their entirety.

FIELD OF THE INVENTION

The invention relates to an agent for cryopreservation of human and animal cells and tissues, which is able to alleviate damages or injuries on the cells and tissues at the time of freezing and thawing the same. This cryopreservation technology is expected to be highly demanded in transplantation medicine where living tissues such as the skin, cornea, pancreatic islets and heart valves need to be cryopreserved, and in regenerative medicine where cells such as hematopoietic stem cells, mesenchymal stem cells, embryonic stem cells, iPS cells (induced pluripotent stem cell) or the like need to be cryopreserved.

BACKGROUND OF THE INVENTION

Cryopreservation techniques at temperatures at or below 0° C. are routinely used for long-time preservation of water-bearing or aqueous materials such as cells and tissues of plants and animals as well as foods. It is known that upon freezing these materials, ice crystals form, resulting uneven concentrations of solutes and contaminants excluded by water molecules, called 'freeze concentration.'

To prevent freeze concentration, various compounds of low molecular weights can be added to the cryopreservation media. For example, dimethylsulfoxide (DMSO), glycerol or the like is added as a freeze-protecting agent to minimize the damages on the cells and tissues, which are otherwise caused by crystallized water in the cells on course of cryopreservation.

Thus, cells are generally suspended in a physiological solution, a culture medium which contains 5-20% cryopreservation agents such as DMSO, glycerin, ethyleneglycol and propylene glycol in a cryotube and preserved at cryogenic temperatures, −80° C. or −196° C.

Among these agents, DMSO is the most effective and frequently adopted, but it is physiologically toxic and known to cause high blood pressure, nausea and vomiting when the cells are transfused to a recipient. Further, the toxicity of DMSO tends to debilitate the cells' survival rates and/or functions after the thawed cells are cultured or transfused into a recipients body.

Glycerin among other agents has lower cryopreservation effects and requires freezing only after keeping cell suspensions at room temperatures or non-freezing low temperatures, or accurately controlling the decreasing temperatures by the use of a program freezer or the like. Moreover, such cryopreservation agents are detrimental to the thawed cells because of their low protective effects on cell survival and functions.

In the cryopreservation of stem cells such as embryonic stem cells or iPS cells or reproductive cells such as sperms, unfertilized or fertilized eggs, a rapid freezing or vitrifaction is performed with high concentrations of cryoprotective agents such gas DMSO, acetamide, propylene glycol and polyethylene glycol. The vitrifaction rapidly renders intracellular water into a vitrified state to avoid injuries or damages on cells caused by the formation of ice crystals. Nevertheless, it is very likely that the cells or the tissues are damaged by the high toxicity of the dense cryopreservation agents; thus, this technique is adopted in only some limited occasions.

In manufacturing pharmaceutical products, foods and ice sculptures for displaying purposes, additives such as sodium chloride or saccharides, glucose and trehalose, are used. Other additives such as antifreeze proteins or antifreeze glycoproteins are also used, which are made from organisms such as plants, fishes and insects (JP2005-126533A (Japan's patent application publication No. 2005-126533) and JP2003-250506A).

In a fuel cell, water is generated on either one of electrodes by an electrochemical reaction. For example, in a proton-exchange membrane fuel cell, water is generated on a cathode electrode; and portion of generated water runs to the anodal side through an electrolyte film. Water would also arise from the condensation of the vapor in a gas going into the cell. These types of water potentially obstruct the gas flow, deplete the supply of the gas itself and eventually decrease a battery performance. These complications can be prevented by treating the surface of a gas separator with hydrophilic coating materials such as proteins thereby limiting the water condensation, but the liquid water even in such a condition is occasionally frozen at low temperatures using other complications. To circumvent this problem, polymer electrolytes with the antifreeze proteins are added to the resin layer, which is then to coat the surface of a polymer electrolyte film (Adler et al. listed in below), but this method has a problem of high cost.

PRIOR-ART DOCUMENTS

Patent Documents

1. JP1998(H10)-511402A: 2. Japan's issued Patent No. 3694730; 3. JP2005-126533A; 4. JP2003-250506A; and 5. JP2008-041596A.

Non-Patent Documents

1. Lovelock J E and Bishop M W H, Nature 183:1394-1395, 1959
2. Polge C, Smith A U, 164:666 Parkes A S, Nature-666, 1949

Nonpatent Literature

3. Miszta-Lane H, Gill P, Mirbolooki M, Lakey J R T, Cell Preserv Technol 5, 16-24, 2007
4. Ha S Y, Jee B C, Suh C S, Kim H S, Oh S K, Kim S H, Moon S Y. Human Reproduction 20, 1779-1786, 2005
5. Yu H N, Lee Y R, Noh E M, et al. INT J. HEMATOL, 87: 189-194; 2008
6. Adler S, Pellozzer C, Paparella M, Hartung T, Bremer S. Toxicol in Vitro 20 265-271, 2006

SUMMARY OF THE INVENTION

Conventional cryopreservation methods including a rapid freezing technique cannot preserve the complete structural integrity of cells or tissues after freezing and thawing; therefore, new cryopreservation materials with low toxicity are greatly demanded. Moreover, DMSO is known to induce differentiation of cells such as HL-60 cells; thus, it is not suited for certain kinds of cells. Anti-freeze proteins and glycoproteins have excellent preserving capabilities, but are too costly (JPY1,300,000 YEN/g) to be used for food materials, not to mention, for cells and tissues.

Present invention is to provide a cryopreservation agent having excellent protective effects and low toxicity for cells or tissues, thus to replace DMSO. The present invention is also to provide an inexpensive and safe cryopreservation agent having a property similar to that of antifreeze proteins and glycoproteins to prevent freeze condensation, thus to enable cryopreservation and lyophilization of materials such as foods and pharmaceutical products.

A cryopreservation liquid according to the invention comprises: substantially 1-50% polyamines having side-chain amino groups; and a physiological solution such as a saline or culture medium.

Various animal cells including human cells, and plant cells are able to be preserved with keeping their survival rate and bioactivity are without using highly toxic DMSO or other conventional cryopreservation agent when the cells are immersed in the cryopreservation liquid and then cryopreserved at −80° C. or under cooling with liquid or vapor nitrogen. Because conventional cryopreservation agents such as DMSO, glycerin, ethylene glycol or the like are not used, toxicity upon the cells are kept to be low and the cells are able to be cryopreserved for an extended period of time without decreasing the cells' bioactivity. Further, the cryopreservation liquid is devoid of protein ingredients such as fetal bovine serum and albumin, therefore, is free of worry of infectious diseases and is not affected by lot-to-lot variations that are occasionally found in pharmaceutical products made from biological materials.

Polyamines having side-chain amino groups, such as ε-poly-L-lysine and polyallylamine, have an affinity with cell membranes due to the side-chain amino groups, thus, is considered to have cell-protecting effects. Polymer compounds having abundant carboxyl groups also have high affinity with water, thus, would help remove intracellular water to the surrounding medium on course of freezing and thereby are expected to have cryopreservation effects. Polymer compounds having both of the amino and carboxyl groups in an adequate ratio are expected to have further improved cryopreservation effects on the cells at a time of freezing. Thus, the invention is to provide a cryopreservation liquid having high effectiveness and high safety, by earnestly investigating conditions or requirements for polymer compounds having cationic groups such as side-chain amino groups, such as poly amino acids, or for polymer compounds having anionic groups such as carboxylic groups as well as for polymer compounds having both of cationic and anionic groups.

A cryopreservation agent according to the invention is less toxic compared to DMSO and requires no washing after thawing of cells or tissues. Thawed cells or tissues then may directly be suspended in a culture medium to immediately start a culturing process.

According to the invention, cryopreservation of cultured cells for experimental use would be made in a stable manner; and moreover, expected to be enabled is preservation by keeping cell functions, of functional cells such as pancreatic islets and stem cells such as ES cells, mesenchymal stem cells and iPS cells. Thus, efficiency in transplantation of these cells is expected to be improved.

By use of non-freezing poly-amino acids according to the invention, deactivation of physiological substances is able to be curbed on course of freezing of water-bearing materials having the physiological substances. Moreover, by use of the non-freezing poly-amino acids, achievable is uniform diffusion of ingredients other than water molecules on course of obtaining frozen products or freeze-dried products by freezing or freeze-drying of the water-bearing or aqueous materials. The frozen product may be Ice cream, sherbet, other frozen sweet, ices for displaying, frozen soup or the like to name a few; and the frozen-dry product may be freeze-dried food or pharmaceutical products, in a powder form, to name a few.

Non-freezing agents according to the invention is also applicable in industrial-use fuel cells as to curb deterioration of their starting-up performance due to freezing of liquid.

BRIEF DESCRIPTION OF DRAWINGS

FIG. 1 is a graph showing a relationship between the percentage of blocked amino groups in ε-poly-L-lysine and the percentage of viable L929 cells cryopreserved by using ε-poly-L-lysine whose amino groups were partially blocked by succinic anhydride;

FIG. 2 is a graph showing a relationship between the concentration of the partially-blocked poly-L-lysine and the percentage of viable L929 cells when cryopreserved by using ε-poly-L-lysine (PLL succinic anhydride 63%) that has been added with succinic anhydride in a molar amount tantamount to 63% of amino groups of the ε-poly-L-lysine;

FIG. 3-1 is a microscopic image showing a culture of L929 cells, which have been frozen in 10% DMSO/fetal bovine serum, then thawed and immediately cultured in a plate for 24 hours without wash or dilution;

FIG. 3-2 is a microscopic image showing a culture of L929 cells, which have been frozen in 7.5% solution of PLL with 63% succinic anhydride, then thawed and immediately transferred onto a plate, for 24 hours without wash or dilution;

FIG. 4 is a set of graphs showing a rat mesenchymal stem cell (RMSC) frozen in 7.5% solution of PLL with 63% succinic anhydride and 10% DMSO/fetal bovine serum and evaluated in terms of their pluripotency to be differentiated into bones, fat bodies, and cartilages. Unfrozen and undifferentiated cells are included for comparison;

DETAILED DESCRIPTION OF THE INVENTION

Figure 5:
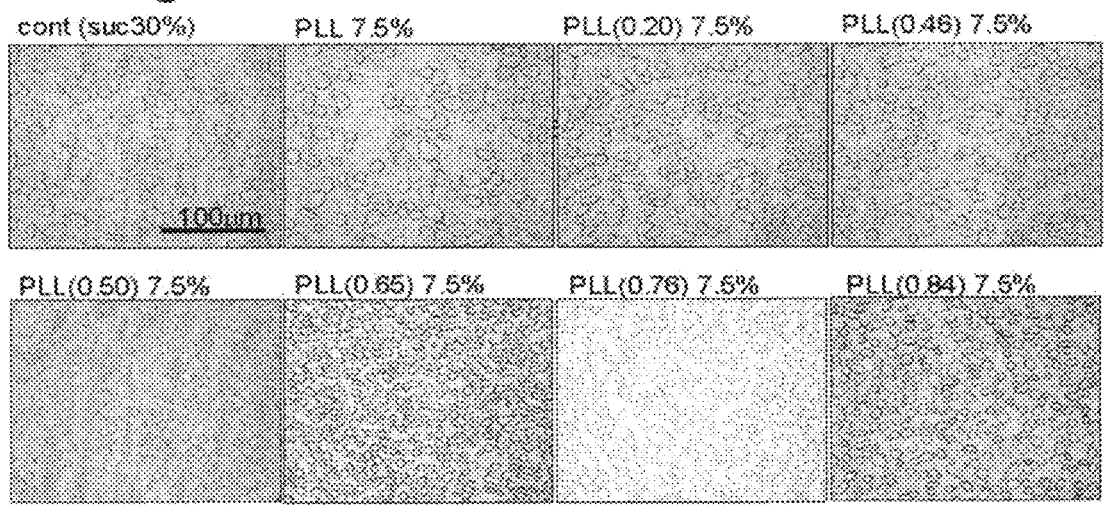
FIG. 5 is a series of microscopic images showing the prevention of ice re-crystallization by adding 0.1-15% PLL (ε-poly-L-lysine) (PLL succinic anhydride 63%) in a 30% sucrose aqueous solution.

A cryopreservation liquid according to the invention is obtained by dissolving a polymer such as poly-lysine in physiological solutions by 1-50 w/w %; preferably by 2-20 w/w %, particularly preferably by 3-15 w/w %, and more preferably by 5-10 w/w %. The physiological solutions to be used are a physiological saline as well as culture media for culturing various cells and tissues. For example, Dulbecco-modified eagle MEM culture medium (DMEM) may be one of the preferable culture media. In place of, or in addition to poly-lysine, polyarylamines may be used. In place of these, or in addition to at least one of these, a compound(s) to be used is/are selected from other polyamines such as amino-group-introduced polyshaccharides, and poly-amino acids such as poly-arginine, poly-glutamic acid and poly-aspartic acid; also a polysaccharide compound(s) that is/are selected from dextran, dextrin, pullulan and chitosan as well as polycarboxylic acid such as polyacrylic acid. Among these polymers, preferable are polymers having a structure obtainable by polymerization of a monomer compound(s) that have both cationic and anionic substituent groups within the same monomer molecules; and especially preferable is poly-amino acids. More specifically, especially preferable is a polymer having a repeating unit that has both amino and carboxyl groups. Poly-lysine to be used can be either $\epsilon$-poly-L-lysine or $\epsilon$-poly-D-lysine or $\alpha$-poly-L-lysine. Cryoprotectant polymers have molecular weights between 100 and 100,000. The most preferable polymers fall into a group of $\epsilon$-poly-L-lysine routinely used as food additives. These are either synthesized by enzymes or produced by the *Streptomyces* fungi and have the average molecular weights of 1000-20,000, and particularly those of 1000-10,000 (www-.chisso.co.jp/fine/jp/polylisin/index.html) with polymerization degrees ranging between 15-35, and those with 20 or lower are attempted to be produced; for examples, as in JP2003-171463A and JP2005-318815A. The average molecular weights or the average polymerization degrees are easily measurable by sodium dodecyl sulfate-polyacrylamide gel electrophoresis (SDS-PAGE), by using an electrophoresis apparatus and AE-6920V type densitograph that are provided by Atto Co., Ltd., for example. Standard protein markers are used for the measurement. The poly-lysine may be heat-treated to increase its molecular weights greater than 30,000 and used as the polymer compound. However, the molecular weight range mentioned above is preferable due to the increasing viscosity with molecular weight. Because the poly-lysine having a free terminal carboxyl group has side-chain primary amino groups, their partial amidation by dicarboxylic anhydrides greatly gives excellent miscibility and solubilization performance described later. Other particularly favorable polymer compounds also adoptable according to the invention are polyarylamines with average molecular weights of 1000-1,000,000, preferably 1000-20,000. For examples, such adoptable polymers are: aqueous solution of the arylamine polymer (PAA-03 of Nitto Boseki Co., Ltd.) added with acetic anhydride or acetic acid; and the partially-methoxy-carbonylated arylamine polymer (PAA-U5000 of Nitto Boseki Co., Ltd.). The arylamine polymer, in same manner with the poly-lysine, has as side-chain groups primary amino groups only, but density of the primary amino group per unit molecular weight is larger in the arylamine polymer than in the poly-lysine. And, when the arylamine is partially carboxylated, obtained polymer compound is considered to act in same manner with partially-carboxylated poly-lysine mentioned later.

Preferably, the amino groups of the polyamine are partially blocked by being carboxylated or acetylated with carboxylic acid anhydride(s). This blockage is done by the carboxylation or acetylation of the amino groups to the degrees of preferably 50-99 mol %, particularly 50-93 mol %, more preferably 50-90 mol %, still more preferably 55-80 mol %, and the most preferably 58-76 mol %. About 50% of the amino group would be blocked by being reacted with 52-53 mol % of anhydrous carboxylic acid on basis of molar amount of the amino groups in the polyamine. In a normal reaction condition, 90-95% of the amino groups would be blocked when reacted with 100 mol % anhydrous carboxylic acid. The blocking rates above or below the above-mentioned ranges would decrease cryopreservation effects. Carboxylic acid anhydrides adoptable herein include acetic anhydride, citric anhydride, succinic anhydride, glutaric anhydride, malic anhydride, fumaric anhydride and maleic anhydride. Among these, succinic anhydride and acetic anhydride are particularly preferred.

However, polyamine with amino groups not blocked as free may gray also be used; thus adoptable are the degrees of carboxylation and acetylation throughout a range of 0-100 mol/mol %. In the present invention, polycarboxylic acid in which a part of the carboxyl groups is aminated may be used. More specifically, polycarboxylic acid may be partially aminated by reacting its carboxyl group with compounds such as diamine, triamine and the polyamine. Adoptable diamines are ethylenediamine and hydrazides such as adipodihydrazide. Reaction of these amino compounds with carboxylic acid is by way of addition reaction with carbodiimide. In such occasion, adoptable is the degree of amination in a range of 0-100 mol/mol %. In same manner with blockade of amino groups, percentage of remaining carboxy groups is preferably in a range of 50-99 mol %, more preferably in a range of 60-97 mol %, in each of which remaining percentage is for aminated carboxylic groups. For example, polyacrylic acid having average molecular weights of 1000-3,000,00, or 1000-10,000 in particular, is used and 1-50 mol % of, preferably 3-40 mol % of, carboxyl groups of the polyacrylic acid are blocked with amines and carbodiimides such as ethylenediamine dihydrazide, or the like. Cryopreservation liquid according to the invention may also contain 0.3-15 w/w %, or 0.1-50 w/w % in particular, of conventional cryoprotectant materials such as DMSO, glycerol, ethyleneglycol, trehalose or sucrose. Because cells are subject to damages caused by the oxidation stress during freezing and thawing, the addition of anti-oxidants to the cryoprotectant is expected to improve its preserving effects. For examples, anti-oxidants such as catalase, peroxidase, superoxide dismutase, vitamin E, vitamin C, polyphenols such as epigallocatechin gallate or glutathione may be used.

The osmotic pressure of the cryopreservation agent according to the invention is 200-1000 mOsm/kg, more preferably is 300-700 mOsm/kg, and further preferably 400-600 mOsm/kg. The cryopreservation agent according to the invention is applicable to the preservation of not only cells but also tissues. Examples of such cells and tissues to be cryopreserved by the cryopreservation agent are cultured cell lines, fertilized eggs of animal and human origin. Further examples are sperm cells, embryonic stem cells, iPS cells, mesenchymal stem cells, haemopoietic stem cells, neuronal stem cells, umbilical cord blood stem cells, hepatocytes, nerve cells, cardiomyocytes, vascular endothelial cells, vascular smooth muscle cells and blood cells. Not only animal or human cells but also plant cells can be included. Tissues and organs that are able to be preserved by the cryopreservation agent according to this invention are skins, nerves, blood vessels, cartilages, cornea, livers, kidneys, hearts and pancreatic islets.

Further, the polymer compounds mentioned above are also applicable to production of frozen or freeze-dried foods or pharmaceuticals by adding the polymer compounds to aqueous or water-bearing materials for the foods or the pharmaceuticals to avoid freeze concentration and to thereby obtain frozen or freeze-dried products, in which ingredients are homogeneously diffused. Specifically adoptable are, a compound selected from a group consisting of ε-poly-L-lysine, α-poly-L-lysine, polyarginine, other polyamine acids, aminated polysaccharides and polyallylamines whose amino groups are blocked with carboxylation or acetylation by being reacted with succinic anhydride, acetic anhydride or other carboxylic acid anhydrides. It is not necessary to use physiological solutions to dissolve the polymer compounds. For example, poly-lysine having partially blocked amino groups, other poly-amino acids or aminated poly-saccharides are added to fore-mentioned water-bearing or aqueous materials for ice cream or freeze-dried foods so that concentration of the polymer compound becomes 1-15%. In this way, freeze concentration is curbed. If succinic anhydride is used for blocking of the polymer groups, excellent effect of curbing the freeze concentration is obtained when succinic anhydride in a molar amount that matches 50-85 mol % of the amino groups is reacted to the polymer, where actual amino-groups-blockage rate is in a range of about 48-80 mol %.

The polymer compounds mentioned in the above are applicable in industrial-use fuel cells so that the polymer compounds are added in the fuel cells to curb deterioration of their starting-up performance that may in otherwise caused by freezing of liquid at a time of starting up. In detail, adoptable are polymer compounds formed of units having amino groups, which are selected from a group consisting of ε-poly-L-lysine, α-poly-L-lysine, polyarginine, other polyamino acids, aminated polysaccharides and polyallylamines; where amino groups of the polymer compound are blocked by carboxylation or acetylation by being reacted with succinic anhydride, acetic anhydride or other carboxylic acid anhydrides; and the polymer compounds may be added to material of surface layer exposed to inside of the fuel cells. For example, the polymer compounds may be incorporated into a material for coating layer, or UV-curable resin liquid ire particular, that forms a surface of separator or solid electrolyte film, by 1-15 w/w %.

EXAMPLES

Shown below are the examples of the invention as well as comparative examples, but the invention is not limited to the examples at below.

Example 1: Preparation of Cryopreservative Solution

A 25% aqueous solution of ε-poly-L-lysine (made by Chisso Corporation; Molecular weight 4000) was used; and a 20% aqueous solution of polyarylamine (Nittobo, molecular weight 5000 [PAA-05L], 15000 [PAA-L], 60000 [PAA-H]) was used. Each of the solution is added with 0-100 mol % succinic anhydride (Wako Pure Chemical Industries) on basis of amino groups of the polyamine polymer to obtain poly-amines having blocked amino groups with different amino-groups-blockage rates. Each poly-amine solution was added to Dulbecco's Modified Eagle Medium (DMEM, Sigma Aldrich) by 0-10 w/w %. On this occasion, pH of the medium was adjusted to 7.0-8.0 with 1N hydrochloric acid or sodium hydroxide solution. Further, the osmotic pressures of the media were measured by a vapor pressure osmometer (Type 5520, Wescor) and adjusted with 10% sodium chloride aqueous solution.

Example 2: Cryopreservation of Cultured Cells

In a cryovial (Simport Plastics), $1 \times 10^6$ cells of each of cell species of L929, MG63, Caco-2 (Japan Sumitomo Pharmaceuticals), Colon26, HT1080, B16F1 and KB cell (ATCC) are suspended in 1 mL of each cryopreservation liquid; and then were frozen in a −80° C. freezer. After one week, the cells were quickly thawed in a 37° C. water bath, washed in DMEM and subjected to cell mortality test with trypan blue dye. The thawed cells were then seeded in 6-well culture plates at $1 \times 10^6$ cells/well, and cell survival rate was evaluated with trypan blue dye after 6 and 24 hours of culturing. A commonly-used cryopreservative, which is 10% DMSO in fetal bovine serum (FBS), was used as a cryopreservation liquid of comparative example.

As shown FIG. 1, when used as the cryopreservation liquid in cryopreserving L929 cells was each 7.5% solution of the poly-lysine (PLL) having been modified by adding 50% or more molar amount of succinic anhydride on basis of amino groups; and then achieved was a cell viability almost same or higher than that of the comparative example using the DMSO solution. A carboxylated poly-lysine (PLLs) having been modified by adding 100% molar amount of succinic anhydride was revealed to have 93% amino-groups-blockage percentage as a result of quantitative measurement of remaining amino groups by ninhydrin and TNBS method. The poly-lysines (PLLs) having been modified by adding 10 mol %, 27 mol %, 45 mol %, 52 mol %; 63 mol % and 79 mol % molar amount of succinic anhydride on basis of amino groups of the poly-lysine were respectively revealed to have 10%, 25%, 43%, 50%, 60% and 76% of amino-groups-blockage percentage. As seen from solutions of the poly-lysine having amino-groups-blockage percentage in a range of 50-93% are revealed to have cryopreservation effect; and particularly high cryopreservation effects were attained by the solutions of the poly-lysine having a 60% of blockage percentage (having been added with 63 mol % of succinic anhydride) and a 76% blockage percentage (having been added with 79 mol % of succinic anhydride). When used was aqueous solutions of polyallylamine having partially blocked amino groups, which is allylamine polymer of molecular weight of 5000 having been reacted with 45-90 mol % of succinic anhydride on basis of molar amount of amino groups in the allylamine polymer; it was also shown that the cell survival rate was improved with increase of the amino-groups-blockage percentage, in same manner with the above.

FIG. 2 shows a relationship between cell survival rate of L929 cells on course of cryopreservation and the concentration of partially-blocked ε-poly-L-lysine; which is modified by adding 63% molar amount of succinic anhydride on basis of amino groups, and which is denoted as "PLL (0.63)" in the Figures and hereinafter referred to as "PLL succinic anhydride 63%" throughout the Description. As seen from FIG. 2, when concentration of the partially-blocked poly-L-lysine or the PLL succinic anhydride 63% is 7.0% or higher; then the cell survival rate was almost same with or higher than that obtained using the DMSO solution. When used was aqueous solutions of polyallylamine having partially blocked amino groups, which is allylamine polymer of molecular weight of 5000 having been reacted with 63-85 mol % of succinic anhydride on basis of molar amount of amino groups; same manner with the above was also shown.

In FIG. 1, range exhibiting best results corresponds to osmotic pressures in a range of 400-600 mOsm/kg as revealed when osmotic pressures of the preservation liquid are obtained. In other words, best preservation effect was obtained when the osmotic pressures are in a range of 400-600 mOsm/kg.

Table 1 shows cryopreservation effect for other species of cells when the cells are cryopreserved in a 7.5% solution of the PLL succinic anhydride 63%. As known from the Table 1, attained for all the cell species are the cell survival rate almost same with or higher than that obtained by the DMSO solution (10% DMSO/fetal bovine serum). The polyallylamine with partially-blocked amino group produced similar results although data are not shown.

TABLE 1

Cryopreservation Effects of 7.5% PLL (0.63) on Various Cells

| Cryopreserved Cell | Survival Rates at 24 hrs after Thawing |
|---|---|
| MG63 | 93.1 ± 2.3 |
| HT1080 | 90.2 ± 4.3 |
| Colon26 | 92.3 ± 2.3 |
| B16F1 | 94.2 ± 0.6 |
| KB | 91.8 ± 0.9 |
| Caco2 | 93.7 ± 1.9 |

Example 3—Toxicity Test

Toxicity test was performed on L929 cells. The cells having been suspended in a culture medium of DMEM with 10% fetal bovine serum are seeded in 96-well plates (1.0× $10^3$ cells/well) and cultured at 37° C. for 72 hours. Thereafter, each of ε-poly-L-lysine and the modified poly-lysines having been added with varying concentrations of succinic anhydride was added to the culture media to attain final concentrations of 0-10%. Then, after the culture for 48 hours, concentration values at 50% cell growth inhibition were measured as $IC_{50}$ MTT assay, relative to cell growth in the culture medium not added with the polymer. Table 2 shows the results; and a preservation liquid of comparative example is the DMSO solution (10% DMSO/fetal bovine serum). As seen from Table 2, $IC_{50}$ values for the PLLs succinic anhydride 58%, 63% and 79% were 2-3 times of that for the DMSO solution; this indicates that the toxicity of the poly-lysine is ½-⅓ of that of the cryopreservation liquids having been generally used. In particular, the $IC_{50}$ values are largest for the PLL succinic anhydride 63% and the PLL succinic anhydride 58%, which are best polymer compounds for high cell survival rate among data shown in FIG. 1.

Meanwhile, the cryopreservation liquid containing the L929 cells was frozen, thawed and directly seeded in 12-well plates and cultured at 37° C. for 24 hours. In detail, the cells were cryopreserved in the 7.5% solution of the PLL succinic anhydride 63% and thawed as in EXAMPLE 2, except that no dilution nor washing was made for the liquid or the cells, and the liquid containing the cells was directly transferred to the plates for culturing. The observation of cells has revealed following. As shown in FIG. 3-1, the cells having been cryopreserved in the DMSO solution (10% DMSO/fetal bovine serum) are apparently round in shape and dead; and as shown in FIG. 3-2, the cells having been cryopreserved in the cryopreservation liquids according to the invention have attached to the plates and survived well. A test result of similarly low toxicity was obtained for the polyallylamine partially blocked at amino group, that is, allylamine polymer of molecular weight of 5000, which has been reacted with 63-85 mol % of succinic anhydride on basis of molar amount of amino groups.

TABLE 2

50% Cell-growth-inhibition Concentration of Cryopreservation Agents on L929

| | $IC_{50}/\%$ |
|---|---|
| DMSO | 2.035 ± 0.017 |
| PLL(0) | 1.194 ± 0.006 |
| PLL(0.44) | 2.025 ± 0.013 |
| PLL(0.58) | >7.500 |
| PLL(0.63) | 6.777 ± 0.005 |
| PLL(0.68) | 3.412 ± 0.097 |
| PLL(0.79) | 4.801 ± 0.017 |

Example 4—Preservation of Mesenchymal Stem Cells

Rat mesenchymal stem cells (RMSC) were cryopreserved. Preservation liquid of the comparative example is 10% DMSO fetal bovine serum; and the preservation liquid used in the example is 7.5% solution of the PLL succinic anhydride 63%, which is denoted as 7.5% PLL (0.63) in FIG. 4.

Table 3 shows that the survival rates of rat mesenchymal stem cells (RMSC) after thawing were almost same for the cryopreservation liquid according to the invention and the DMSO solution. DMEM added with 7.5% polyallylamine partially blocked at amino group (allylamine polymer of molecular weight of 5000, to which 63-85 mol % succinic anhydride equivalent to the amino group content was reacted) exhibited similarly high cell survival rates.

TABLE 3

Cryopreservation Effect to Rat Mesenchymal Stem Cell

| | Immediately | 6 hours later | 24 hours later |
|---|---|---|---|
| 10% DMSO | 92.3 ± 4.3 | 88.3 ± 1.1 | 92.8 ± 3.5 |
| 7.5% PLL (0.63) | 95.4 ± 3.8 | 92.9 ± 2.0 | 95.7 ± 1.3 |

The cells were cryopreserved and thawed as described in Example 2; and they were induced to differentiate into bone cells, fat cells and chondrocytes to evaluate their differentiation potentials. FIG. 4 shows that the cells' multipotency was maintained to be almost same with that of the cells not frozen and with that of the cells cryopreserved and thawed in the DMSO solution. Image data of colored microphotograph images were subjected to color separation into three primary colors of red, green and blue; and only the red color part is shown in FIG. 4. Thus, the red color in the color images is translated to white color; and blue color in the color images is translated to black. The differentiation potential to bone cells was evaluated by evaluating of depositing of calcium by way of staining with alizarin red S; and resultantly, red staining was made for each of the samples. As seen from top-rank images in FIG. 4, all the images of the differentiated cells are presented as similarly dilute or low-gray-scale monochrome patterns as compared with that of undifferentiated one. The dilute monochrome patterns indicate that the colored microphotograph images have a reddish tint over their whole areas. Meanwhile, the cells cryopreserved in each of the cryopreservation liquids show alkaline phosphatase activity as high as those not frozen. Differentiation potential into fat cells was evaluated by staining of fat droplets with oil red O. The fat droplets stained as red were observed for microphotograph images of the cells cryopreserved in each of the cryopreservation liquids. The fat droplets appear in middle-rank images of FIG. 4, as circular or ellipsoidal patterns having low gray scales and diameter of dozens of micrometers. Differentiation potential into cartilage cells was evaluated by staining of proteoglycans in cell aggregates, with Alcyan blue. Resultantly, the proteoglycans stained to be blue were observed for microphotograph images of the cells cryopreserved in each of the cryopreservation liquids, in same manner with that of the cells not frozen. The proteoglycans appear in bottom-rank images of FIG. 4, as deep black portions. When used as a preservation liquid is DMEM added by 7.5% with the polyallylamine partially blocked at amino group (allylamine polymer of molecular weight of 5000, to which 63-85 mol % succinic anhydride equivalent to the amino group content was reacted); then differentiation potentials of the cells were maintained even after the freezing in similar manner as the above.

Example 5—Preservation of Cord Blood

Umbilical cord blood was collected from human umbilical cord by a 7 mL plastic vacuum blood sampling tube (Venoject II, Terumo Corporation) loaded with 10.5 mg anticoagulant (EDTA2Na). Subsequently, the cord blood, into which the PLL succinic anhydride 63% was added so that its concentration becomes 7.5% as denoted as 7.5% PLL (0.63), was cryopreserved in a freezer at −80° C. for three months. Then the cord blood was quickly thawed in a water bath at 37° C., and a sample of cord blood without dilution was analyzed with respect to the expression of the surface marker, CD34, by flow cytometry. The number of hematopoietic cells expressing CD34 was measured according to the standard method described in the literature (A. Higuchi et al., J. Biomed. Mater. Res., 68A, the fixed method of 34-42 (2004)). Thus the number of CD34-expressing hematopoietic cells was estimated according to the protocol in the manual (International Hemotherapeutics and Transplantation Society ISHAGE guideline) using Stem-Kit (Beckman-Coulter Corporation). Even after the three months of cryopreservation, number of counted cells of the CD34-expressing hematopoietic cells was estimated to be about 70% of that on the first day when the cord blood was added with the PLL succinic anhydride 63% was added by 7.5%; whereas, when the cord blood in a state of 10% DMSO solution was cryopreserved, number of the CD34-expressing hematopoietic cells was estimated to be about 20% of that on the first day. Thus, it was revealed that the CD34-expressing hematopoietic cells are able to be preserved in undifferentiated state for an extended period of time when the cord blood is stored in the preservation liquid added with the ε-poly-L-lysine.

These results indicate that the cryopreservation liquid according to an embodiment of the invention is remarkably excellent in preserving effects on cord blood.

Example 6—Antifreeze Protein Activity

With respect to the PLL (ε-poly-L-lysine) and the succinic-anhydride modified PLL, investigated is antifreeze protein activities, or capabilities of curbing recrystallization of ice. Antifreeze proteins are known to have various special activities are known and to cause thermal hysteresis, curbing of recrystallization growth of ice, and morphological alteration of ice crystal to hexagonal one or bipyramidal one. Please see JP2005-126533A, JP2003-250506A and JP2008-041596A.

A 30% sucrose aqueous solution was added with non-modified PLL and the PLL succinic anhydride 20%, PLL succinic anhydride 46%, PLL succinic anhydride 50%, PLL succinic anhydride 65%, PLL succinic anhydride 76% and PLL succinic anhydride 84%, by 1-15%. Actual amino-groups-blockage rates for these succinic-anhydride modified PLLs were measured by fore-mentioned method and were revealed to be about 0.20, 0.43, 0.48, 0.62, 0.73 and 0.80 respectively. Four micro liters (4 µL) of solution of each of the non-modified PLL and the modified PLLs was putted onto a glass plate and covered with another glass plate, then was placed on a temperature-controlled stage of a microscope, or rapid cooling stage 10002L of a company named as Linkam; and was rapidly cooled to −30° C. to induce formation of ice crystals. Subsequently, temperature of the stage was gradually raised, and then was kept as left at −9° C. for 30 minutes; and on course of it, growth of ice crystals were observed by the microscope. As seen from a series of microphotographs of FIG. 5, it was revealed from the results that effect of curbing ice recrystallization is given to the PLL by introducing of carboxyl groups up to 50% or more of the amino groups. FIG. 5 shows results where the non-modified PLL and modified PLLs are added to become 5 weight percentage in the solutions whereas 1% through 15% concentration of the PLL succinic anhydride 50% (PLL (0.50)) through the PLL succinic anhydride 84% (PLL (0.84)) were revealed to be effective in curbing of the recrystallization of ice.

Figure 6:
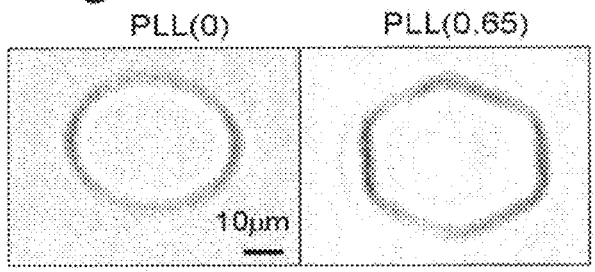
FIG. 6 is a microscopic image showing a crystal structure in the frozen 5% solution of PLL (ε-poly-L-lysine) without succinic anhydride, and 5% solution of PLL with 63% succinic anhydride).

Subsequently, on the rapid cooling stage, investigated was morphology of ice crystals of the 5% solution of non-modified PLL and the 5% solution of the modified PLL (the PLL succinic anhydride 65%). In detail, at first, the solution was rapidly cooled to −30° C. to induce formation of abundant ice crystals; and then temperature of the solution was raised at a rate of 0.02° C./minute up to a temperature at which one ice crystal having about 10 µm diameter is existed in a viewing range of the microscope. As shown in microscopic image of FIG. 6, the ice crystals in the solution of the succinic-anhydride modified PLL were revealed to have shapes of hexagonal crystals. It should be noted that such hexagonal crystals were shown if and when concentration of either of the PLL succinic anhydride 50% (PLL (0.50)) through the PLL succinic anhydride 84% (PLL (0.84)) was in a range of 1% through 15%. The heat hysteresis, which is difference between a melting temperature and a crystal-growth-starting temperature and one of characteristic properties of the antifreeze proteins, was obtained for the succinic-anhydride modified PLL up to 0.1° C. at maximum. This reveals that the antifreeze protein activity is obtainable by introducing carboxylic acid groups onto the amino groups of the PLL by 50 molar % or more of the amino groups.

Example 7 Preservation of Food

Figure 7:
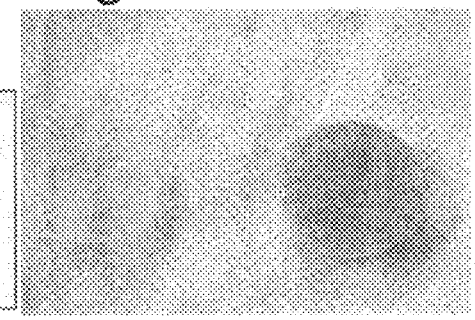
FIG. 7 is photograph (1) of freeze-dried agar gels. The gel on the left is additive-free, and one on the right has 5% PLL with 63% succinic anhydride.

Curbing of Freeze Concentration—Frozen-Thawed Agar Gel:

Agar powder (Naraitesque Co.; 1st grade reagent) was added with the PLL succinic anhydride 63%; and then 5% solution was prepared. This solution is added with red ink, putted into a plastic bottle and then frozen at −20° C.; and subsequently thawed at a room temperature. Obtained result is shown in FIG. 7; right-hand-side gel was obtained with 5% addition of the PLL succinic anhydride; and left-hand-side gel was obtained with no addition. The left-hand-side gel on the view shows clear division between a red-colored opaque part on view's top-side half and a translucent part on view's bottom-side half, through which a mesh pattern of paper towel appears and which nevertheless induces a shadow on view's top-right neighbor. Meanwhile, the right-hand-side gel obtained with addition of the PLL succinic anhydride shows a red color evenly throughout whole of the gel; and thus indicates that freeze concentration has been curbed.

Figure 8:
FIG. 8 is photograph (2) of frozen-thawed agar gels. The concentrations of PLL with 63% succinic anhydride are 0% (left), 1% (middle) and 3% (right).

Freeze-Dried Agar Gel:

Agar powder (Naraitesque Co.: 1st grade reagent) was added with the PLL succinic anhydride 63%, actual amino-groups blockage ratio of which is 0.6, by 0%, 1% and 3%. Solution was putted into a plastic bottle and then frozen at −20° C.; and subsequently freeze-dried by vacuuming at 1 Torr for 2-3 days to obtain a freeze-dried agar gel. Photograph image of obtained freeze-dried product is shown in FIG. 8. A freeze-dried agar gel obtained with 0% addition of the PLL succinic anhydride on left-hand side of the view shows a volume shrinkage to about one third of the original whereas freeze-dried agar gels obtained with 1% and 3% addition of the PLL succinic anhydride (center and right-hand side of the view) show only a small extent of volume shrinkage. This results indicate that freeze-drying of the solution containing the non-freezing polyamino acid according to the invention leads to drying that is efficient and keeps duality of the product.

The invention claimed is:

1. A method for preserving foods or pharmaceuticals, comprising: suspending or immersing foods or pharmaceuticals in a cryopreservative liquid; and then, freezing the cryopreservative liquid as well as the foods or pharmaceuticals; wherein
said cryopreservative liquid is an aqueous solution comprising 1-15% by weight relative to the total weight of the cryopreservative liquid of one or more polyamine polymer compounds comprising one or more polymers of units having side-chain amino groups, said polymers of units being ε-poly-L-lysine; and wherein
48-80 mol % of the amino groups, other than those forming amino-acid-to-amino-acid linkages, of said polymer compounds are blocked with a carboxylic anhydride to form pendant moieties, each of which is linked to the main chain of the polymer of units via an amide linkage and has a free carboxylic acid group.

2. The method according to claim 1, further comprising freeze-drying of the cryopreservative liquid as well as the foods or pharmaceuticals.

3. The method according to claim 1, wherein said polymer compound is ε-poly-L-lysine having number-average molecular weight in the range of 1000-20,000.

4. The method according to claim 1, wherein remaining side-chain amino groups or remaining side-chain and terminal amino groups of the polymer compound are not blocked by covalent bonding.

* * * * *